(12) United States Patent
Amiot et al.

(10) Patent No.: US 9,495,509 B2
(45) Date of Patent: Nov. 15, 2016

(54) METHOD AND SYSTEM FOR PLANNING/GUIDING ALTERATIONS TO A BONE

(71) Applicant: ORTHOSOFT, INC., Montreal (CA)

(72) Inventors: Louis-Philippe Amiot, Hampstead (CA); Yannick Boutin, Montreal (CA); Yonik Breton, Montreal (CA); Karine Duval, Montreal (CA); Herbert Andre Jansen, Montreal (CA); Benoit Pelletier, Laval (CA); Catherine Proulx, Verdun (CA); Alain Richard, Lachine (CA); Myriam Valin, Laval (CA); Joel Zuhars, Warsaw, IN (US)

(73) Assignee: ORTHOSOFT, INC., Montreal (CA)

( * ) Notice: Subject to any disclaimer, the term of this patent is extended or adjusted under 35 U.S.C. 154(b) by 364 days.

(21) Appl. No.: 14/157,043

(22) Filed: Jan. 16, 2014

(65) Prior Publication Data
US 2014/0316545 A1 Oct. 23, 2014

Related U.S. Application Data

(60) Division of application No. 13/588,543, filed on Aug. 17, 2012, now Pat. No. 8,718,820, which is a continuation of application No. 12/410,884, filed on Mar. 25, 2009, now Pat. No. 8,265,790.

(60) Provisional application No. 61/039,184, filed on Mar. 25, 2008, provisional application No. 61/100,173, filed on Sep. 25, 2008.

(51) Int. Cl.
*G06F 17/50* (2006.01)
*G01C 21/16* (2006.01)
(Continued)

(52) U.S. Cl.
CPC ......... *G06F 17/5086* (2013.01); *A61B 17/155* (2013.01); *A61B 17/157* (2013.01);
(Continued)

(58) Field of Classification Search
CPC .................................... G06F 17/5086
USPC ........... 33/512, 333, 783, 784, 807, 558.01, 33/558.2
See application file for complete search history.

(56) References Cited

U.S. PATENT DOCUMENTS 4,571,834 A * 2/1986 Fraser .................. A61B 5/1107
33/1 PT
4,872,268 A * 10/1989 Perrault .................. A61B 5/103
33/391
(Continued)

FOREIGN PATENT DOCUMENTS

EP 1 749 473 2/2007
WO WO 2004017842 A2 * 3/2004 ........... A61B 17/154
(Continued)

OTHER PUBLICATIONS

I. Scott MacKenzie et al. "A Two-Ball Mouse Affrods Three Degrees of Freedom", Late Breaking/Short Talks, CHI 97, Mar. 22-27, 1997, pp. 303-304.

*Primary Examiner* — Christopher Fulton
(74) *Attorney, Agent, or Firm* — Norton Rose Fulbright Canada LLP

(57) ABSTRACT

A computer-assisted surgery system for guiding alterations to a bone, comprises a trackable member secured to the bone. The trackable member has a first inertial sensor unit producing orientation-based data. A positioning block is secured to the bone, and is adjustable once the positioning block is secured to the bone to be used to guide tools in altering the bone. The positioning block has a second inertial sensor unit producing orientation-based data. A processing system providing an orientation reference associating the bone to the trackable member comprises a signal interpreter for determining an orientation of the trackable member and of the positioning block. A parameter calculator calculates alteration parameters related to an actual orientation of the positioning block with respect to the bone.

3 Claims, 14 Drawing Sheets

(51) Int. Cl.
*A61B 17/15* (2006.01)
*A61B 17/00* (2006.01)

(52) U.S. Cl.
CPC .............. *A61B 34/20* (2016.02); *G01C 21/16* (2013.01); *A61B 2017/00115* (2013.01); *A61B 2017/00725* (2013.01); *A61B 2034/2048* (2016.02)

(56) References Cited

U.S. PATENT DOCUMENTS

| | | | |
|---|---|---|---|
| 4,986,280 A * | 1/1991 | Marcus | A61B 5/103 33/512 |
| 5,327,907 A * | 7/1994 | Fischer | A61B 5/103 33/558.01 |
| 5,430,954 A * | 7/1995 | Best | A61B 5/0053 33/784 |
| 5,971,976 A | 10/1999 | Wang et al. | |
| 6,122,538 A | 9/2000 | Sliwa et al. | |
| 6,786,877 B2 | 9/2004 | Foxlin | |
| 7,065,393 B2 | 6/2006 | Sati et al. | |
| 7,277,594 B2 | 10/2007 | Hofstetter et al. | |
| 7,954,251 B2 * | 6/2011 | Nunes | A61B 5/1071 33/471 |
| 8,718,820 B2 * | 5/2014 | Amiot | A61B 19/5244 606/130 |
| 9,021,712 B2 * | 5/2015 | Caritu | B25J 5/00 33/503 |
| 2002/0103610 A1 | 8/2002 | Bachmann et al. | |
| 2004/0039396 A1 | 2/2004 | Couture et al. | |
| 2004/0243148 A1 | 12/2004 | Wasielewski | |
| 2005/0113646 A1 | 5/2005 | Sotos et al. | |
| 2005/0251026 A1 | 11/2005 | Stone | |
| 2006/0015018 A1 | 1/2006 | Jutras et al. | |
| 2007/0032723 A1 | 2/2007 | Glossop | |
| 2007/0032748 A1 | 2/2007 | McNeil | |
| 2007/0287901 A1 | 12/2007 | Strommer et al. | |
| 2007/0287911 A1 | 12/2007 | Haid et al. | |
| 2008/0051910 A1 | 2/2008 | Kammerzell et al. | |
| 2008/0065084 A1 | 3/2008 | Couture et al. | |
| 2009/0187120 A1 | 7/2009 | Nycz | |
| 2009/0300811 A1 | 12/2009 | Lundahl | |
| 2010/0016705 A1 | 1/2010 | Stone | |
| 2011/0031735 A1 | 2/2011 | Gerigk et al. | |
| 2012/0074876 A1 | 3/2012 | Redler | |

FOREIGN PATENT DOCUMENTS

| | | | | |
|---|---|---|---|---|
| WO | WO 2009111888 A1 * | 9/2009 | ............... | A61B 5/06 |
| WO | WO 2009117832 A1 * | 10/2009 | ......... | A61B 19/5244 |
| WO | WO 2012012863 A1 * | 2/2012 | ......... | A61B 19/5244 |
| WO | WO 2012113054 A1 * | 8/2012 | ......... | A61B 19/5244 |

* cited by examiner

METHOD AND SYSTEM FOR PLANNING/GUIDING ALTERATIONS TO A BONE

CROSS-REFERENCE TO RELATED APPLICATIONS

This patent application is a divisional of U.S. Pat. No. 8,718,820, filed on Aug. 17, 2012 which is a continuation of U.S. Pat. No. 8,265,790, filed on Mar. 25, 2009 which claims priority on U.S. Provisional Patent Application No. 61/039,184, filed on Mar. 25, 2008, and U.S. Provisional Patent Application No. 61/100,173, filed on Sep. 25, 2008.

FIELD OF THE APPLICATION

The present application relates to computer-assisted surgery systems and, more particularly, to instrumentation used for tracking or positioning surgical tools during computer-assisted surgery.

BACKGROUND OF THE ART

Tracking of surgical instruments or tools is an integral part of computer-assisted surgery (hereinafter CAS). The tools are tracked for position and/or orientation in such a way that information pertaining to bodily parts is obtained. The information is then used in various interventions (e.g., orthopedic surgery, neurological surgery) with respect to the body, such as bone alterations, implant positioning, incisions and the like during surgery.

The tracking systems may use different technologies, such as mechanical, acoustical, magnetic, optical and RF tracking. Depending on the technology used, different types of trackable references are fixed, permanently or temporarily, to the item that needs to be tracked. For instance, during Total Knee Replacement (TKR) surgery, trackable references are fixed to the limbs and to the different surgical instruments, and these trackable references are tracked by the tracking system. The CAS system calculates position and orientation data associated with the tracking, and the information displayed by the computer is used by the surgeon to visualize the position of the instrument(s) being manipulated with respect to the limbs, or in numerical values.

Two types of tracking systems are commonly used. The active tracking systems provide a transmitter as trackable reference on the tool to be tracked, which transmitter emits signals to be received by a processor of the CAS system, which will calculate the position and/or orientation of the tool as a function of the signals received. The transmitters of the active tracking systems are powered, for instance by being wired to the CAS system or by being provided with an independent power source, so as to emit signals.

Passive tracking systems do not provide active transmitters on the tools as trackable references. The CAS system associated with passive tracking has an optical sensor apparatus provided to visually detect optical elements on the tools. The optical elements are passive, whereby no power source is associated therewith.

In order to obtain values for position and/or orientation, the optical elements must be in the line of sight of the optical sensor apparatus. Accordingly, with passive tracking systems, surgery takes place in a given orientation as a function of the required visibility between the optical sensor apparatus and the optical elements.

The trackable references currently used, whether active or passive, have a noticeable size depending on the technology used. For an electromagnetic system, a casing is wired to the CAS system and is secured to the instrument or to the patient. For an optical system, a trackable reference generally comprises at least three optical elements in order to provide six degrees of freedom (DOF). For instance, the optical elements are light sources wired to the CAS system and forming a scalene triangle. The light sources can be individually fixed or assembled on a base. In this second construction, the assembly is large and obstructive.

As an alternative, passive reflector spheres or patches can be used instead of light sources, and a light source is used to illuminate them (in the infrared spectrum).

Some factors must be considered when selecting a type of tracking system: the presence of wires in sterile zones for active trackable references; a line of sight required for navigation when using optical tracking; the size of the trackable references in order to deliver the required precision during surgery; the necessity for the surgeon to visualize a computer screen for intraoperative alignment information; the necessity for the surgeon to digitize landmarks on bones in order to build coordinate systems; the difficulty in integrating current optical or radio-frequency sensors in disposable instruments (such as cutting guides) because of their volume. Electromagnetic tracking devices are subject to distortions introduced by conventional orthopaedic instruments which may be difficult to detect and may cause a loss in accuracy. These tracking devices are used as general data input devices, digitizing points on patients or surgical instruments in order to compute planes, point-to-point distances, planar angles, planar distances, etc., required during CAS.

No alternate miniaturized technologies with fewer than 6 DOF is currently used in orthopaedic CAS, while still providing the crucial information required to install orthopaedic implants. Such technology could be directly integrated to instruments, thus reducing the need for an external tracking system, thereby resulting in enhanced ease-of-use.

SUMMARY OF THE APPLICATION

It is therefore an aim of the present application to provide a method and system for planning/guiding alterations to bones which address issues associated with the prior art.

Therefore, in accordance with the present disclosure, there is provided a computer-assisted surgery system for planning/guiding alterations to a bone in surgery, comprising: a trackable member adapted to be secured to the bone, the trackable member having a first inertial sensor unit producing orientation-based data for at least two degrees of freedom in orientation of the trackable member; a positioning block adapted to be secured to the bone, with at least an orientation of the positioning block being adjustable once the positioning block is secured to the bone to reach a selected orientation at which the positioning block is used to guide tools in altering the bone, the positioning block having a second inertial sensor unit producing orientation-based data for at least two degrees of freedom in orientation of the positioning block; a processing system providing an orientation reference between the bone and the trackable member and comprising: a signal interpreter for determining an orientation of the trackable member and of the positioning block from the orientation-based data; and a parameter calculator for calculating alteration parameters related to an actual orientation of the positioning block with respect to the bone as a function of the orientation reference and of the orientation of the positioning block.

Further in accordance with the present disclosure, there is provided a method for planning/guiding alterations to a bone comprising: providing a trackable member secured to a bone, the trackable member having a first inertial sensor producing orientation-based data for at least two degrees of freedom in orientation for the trackable member; providing a positioning block secured to the bone, the positioning block having an inertial sensor unit producing orientation-based data for at least two degrees of freedom in orientation for the positioning block, an orientation of the positioning block being adjustable with respect to the bone; determining an orientation reference of the bone at least from the orientation-based data of the trackable member; and calculating bone alteration parameters from the orientation-based data of the positioning block with respect to the orientation reference of the bone.

Still further in accordance with the present disclosure, there is provided a caliper for determining a dimension of an object, comprising: a base having a known base length; arms pivotally mounted to ends of the base, the arms each having a known arm length, and each having a free end used to identify a limit point of the object to measure; an inertial sensor unit secured to at least the arms, the inertial sensor unit producing orientation data pertaining to at least one degree of freedom in orientation of the arms in a plane in which the arms and the base lie; whereby the dimension between limit points is calculated from the known base length and arm lengths and from the orientation data of the arms.

DESCRIPTION OF THE PREFERRED EMBODIMENTS

Figure 5:
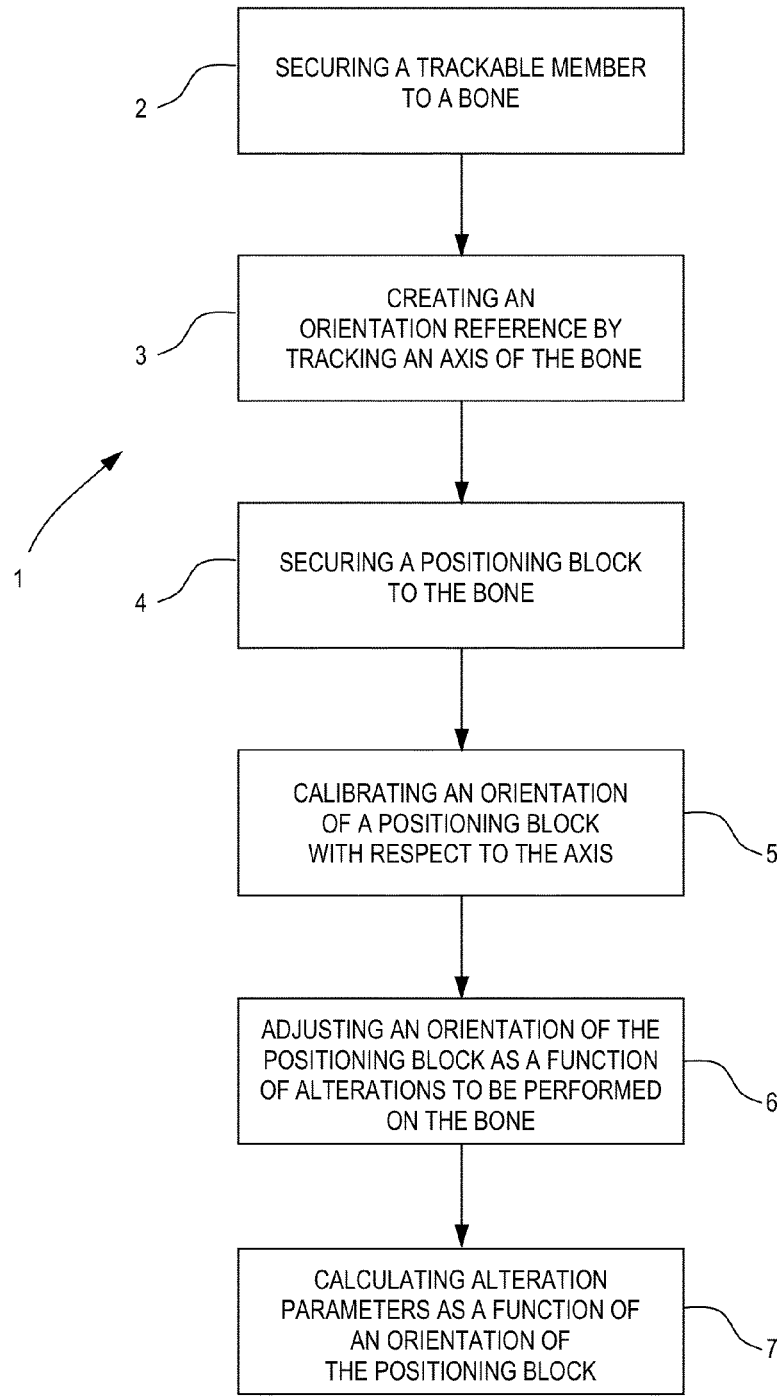
FIG. 5 is a flow chart illustrating a method for planning/guiding alterations to a bone in computer-assisted surgery in accordance with an embodiment of the present disclosure.

Referring to FIG. 5, a method for planning/guiding alterations to a bone is generally illustrated at 1. The method 1 is used for instance to subsequently alter bones in knee replacement surgery, in view of installing knee joint implants on the femur and/or on the tibia.

Figure 6:
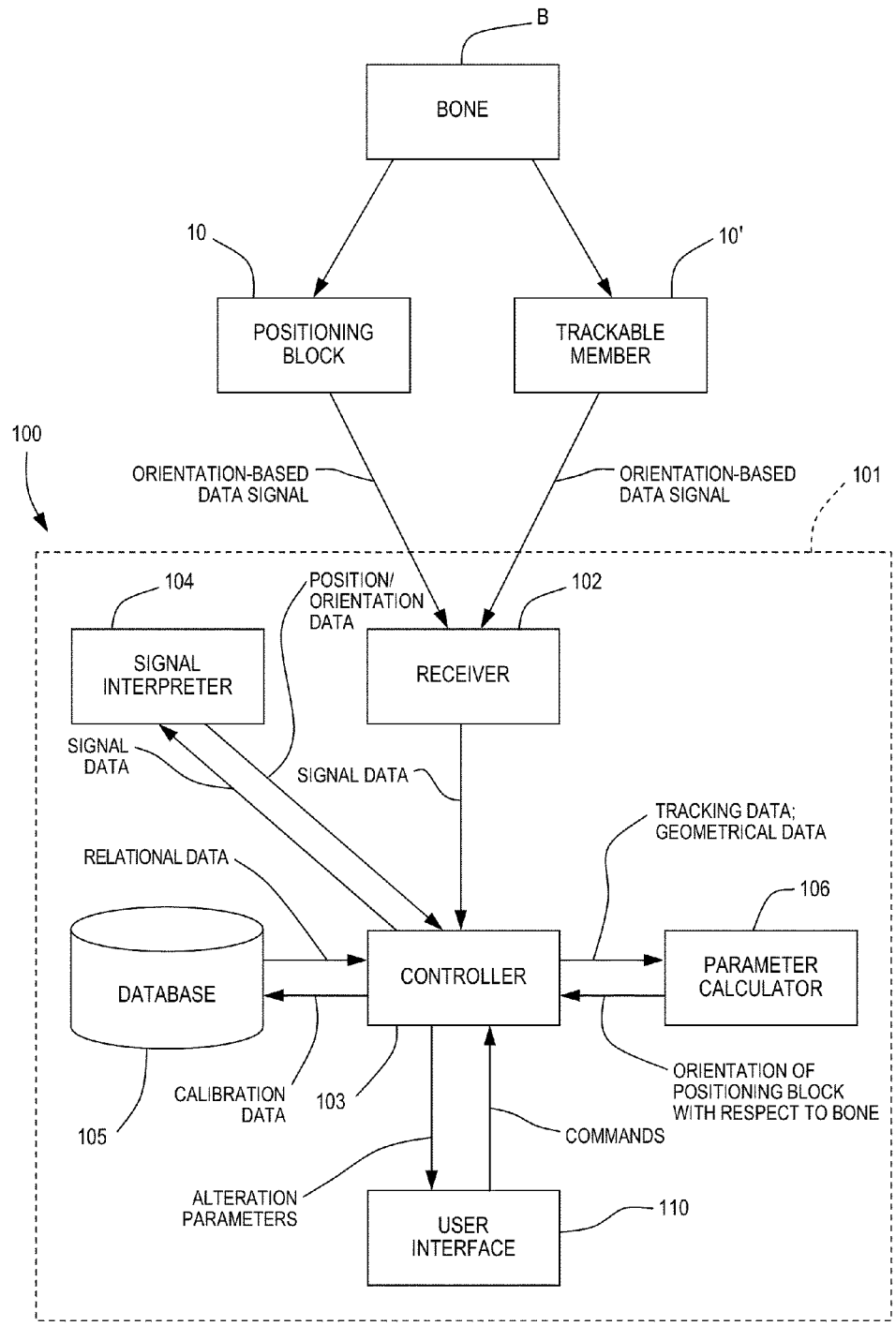
FIG. 6 is a block diagram illustrating a computer-assisted surgery system for planning/guiding alterations to a bone in accordance with another embodiment of the present disclosure.

Referring concurrently to FIGS. 5 and 6, the method 1 uses a positioning block 10 (i.e., navigated cutting block), such as the positioning blocks defined in United States Publication No. 2008/0065084, and United States Publication No. 2004/0039396, by the current assignee. The subject matter of both these references is incorporated herein by reference. In both these references, the positioning block is provided with an optical tracker member that is visually tracked to serve as a guide for subsequent alterations to the bone.

The present application features tracking members with inertia-based tracking circuitry instead of the optical tracker member (i.e., hereinafter inertial sensors). The tracking circuitry features micro-electromechanical sensors (MEMS), gyroscopes, accelerometers or other types of sensors (electrolytic tilt sensors, compasses) to detect orientation changes, for instance in the positioning block, instead of electromagnetic (EM) transmitter/receiver coils or optically-detectable members. In one embodiment, the sensors are connected to an embedded processor on the positioning block. The following sensors are considered, amongst other possibilities: tri-axial gyroscopic sensors in an orthogonal or semi-orthogonal configuration as well as tri-axial accelerometer sensors in an orthogonal or semi-orthogonal configuration. The method for computing angles between the cutting block and the bone is different from conventional tracking systems: planar information and optionally position information is obtained directly from the MEMS devices rather than having to compute this information from the optical tracking data. In other words, the inertial sensors provide at least two degrees of freedom in orientation, and optionally up to three degrees of freedom in position.

Figure 1:
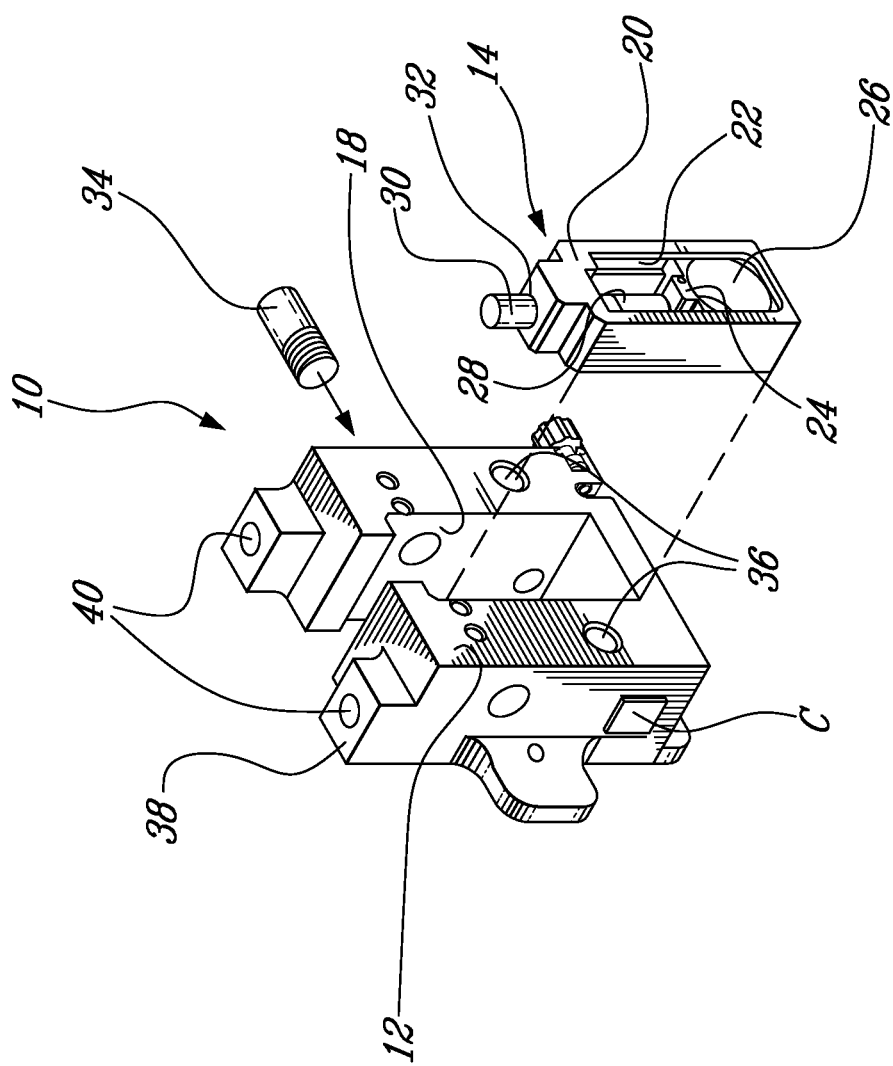
FIG. 1 is an exploded perspective view of a trackable CAS universal positioning block according to an embodiment.

By way of example, referring to FIG. 1, an embodiment of the universal positioning block assembly 10 comprises generally a cutting tool guide element or guide body member 12, a mounting member 14 and a MEMS tracking circuit C. The main guide body 12 comprises a large central aperture 18 for receiving the mounting member 14 therein. The guide body 12 comprises cutting guide surfaces, such as the two drill guide holes 36, which extend through the guide body 12. The guide body 12 also includes means for engagement to a cutting guide, comprising, for example, a pair of mounting points 38 having peg holes 40 that are disposed on the top of the guide body, permitting engagement with another drill/cutting guide block for example.

The mounting member 14 comprises a translation mechanism including a fastener receiving mount element 24, which slides within the central guide slot 22 disposed within the mounting member body 20. The fastener mount element 24 comprises a semi-spherically shaped bowl 26 which has a through hole at the bottom thereof. The fastener mount element 24 is displaced relative to the mounting member body 20 by an endless screw 28, engaged to the fastener mount element and extending through an inside-threaded hole 32 in the mounting member body 20. The translation screw 28 is actuated by a screw head 30 such that rotation of the screw head 30 causes the fastener mount element 24 to be translated within the central guide slot 22. The translation, or elevation, screw 28 thereby enables the entire positioning block to be raised or lowered, for instance along an anterior-posterior axis when engaged to a distal end of a femur. The entire mounting member 14 additionally slides within the central aperture 18 of the guide body 12, generally permitting the guide body to be displaced along a proximal-distal axis when the positioning block is engaged to a distal end of a femur. A friction locking screw 34 extends through the side of the guide body and engages the mounting member 14, such that it can be retained in a selected position relative to the guide body 12.

Figure 3:
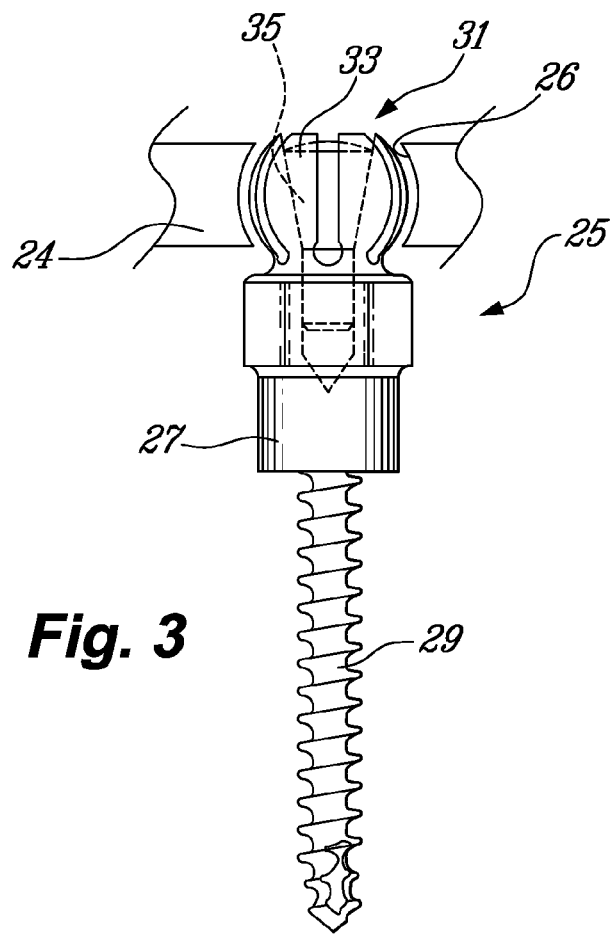
FIG. 3 is a side elevation view of a polyaxial mounting screw element used to fasten the universal positioning block of FIG. 2 to a bone element.

A polyaxial mounting screw 25, as best seen in FIG. 3, is used to mount the universal positioning block 10 to the bone. The polyaxial screw 25 comprises generally a main screw body 29 having threads on the outside, a shoulder portion 27, and a spherical screw head 31 having a plurality of integrally formed individual petal elements 33. A central conical screw 35 is inserted through the center of the screw head, and when engaged therein, forces the petal elements 33 outwards, thereby causing them to press against the semi-spherical surface 26 of the fastener mount element 24. This consequently immobilizes the fastener mount element 24 in position on the spherical polyaxial screw head 31, fixing it in position thereon. The petal elements 33 are slightly elastically deflectable and the polyaxial screw head 31 is sized such that the petal elements are forced slightly radially inward when the fastener mounting element is pressed down overtop, and engaged to the screw head. This ensure that once snapped in place, the fastener mount element 24, and subsequently the entire positioning block assembly, can freely rotate about the polyaxial screw head in three rotational degrees of freedom. Once the positioning block is aligned in the desired position, the conical screw 35 at the center of the polyaxial screw head 31 can be tightened, thereby rotationally fixing the guide block assembly in place on the polyaxial mounting screw 25. When the term polyaxial screw is used herein, it is to be understood that it comprises preferably a screw having a substantially spherical head. The spherical head permits a ball and socket type joint to be created, when an element with a receiving socket is engaged with the ball head of the polyaxial screw. The spherical head preferably, but not necessarily, includes the individual petal elements that are displaceable by the central conical screw in order to provide a locking mechanism. Other mechanisms to lock the member with the receiving socket in a selected position on the head of the screw are equivalently possible.

As described hereinafter, the positioning block 10 with MEMS is used in combination with another MEMS tracker member 10' that performs the dynamic tracking of the bone B. The MEMS tracker member 10' is secured directly to the bone B (or soft tissue) to be in a fixed relation with the bone B.

In another embodiment illustrated for instance in FIGS. 12 and 13, the positioning block 10 with MEMS is used in an independent manner, where the mechanical axis measurements described hereinafter, or a portion thereof, are determined directly by the positioning block pinned on the bone, instead of through the use of the tracking member 10' which may or may not be present in this embodiment. Tracking circuitry (equivalent to the tracking member 10') is provided on both the fixed portion of the positioning block (i.e., fixed to the bone), and the movable portion of the positioning block. Once the mechanical axis measurements are determined, the positioning block would then be used to perform the planned bone cut(s), as further described below. Therefore, as the positioning block 10 is secured to the bone, both the MEMS fixed to the bone and the MEMS of the movable portion of the positioning block 10 are installed.

Now that the MEMS positioning block 10 and the MEMS tracker member 10' are defined, the method 1 is described as used to plan alterations on the femur at the knee, with reference being made to FIG. 5.

According to step 2 of the method, the MEMS tracker member 10' is secured to the femur.

According to step 3 of the method, at least one axis of the femur is digitized. For the femur, the axis is, for instance, the mechanical axis passing through a center of the femoral head and a central point between the condyles at the knee. The axis can also be a rotational axis of the bone, pointing either in a medio-lateral or antero-posterior direction.

In order to digitize the mechanical axis, the femur is rotated about its mechanical axis, and the movements are sensed by the MEMS tracking member 10' on the femur. By the sensing data collected by the MEMS tracker member 10' secured to the femur, a computer-assisted surgery system digitizes the mechanical axis of the femur and tracks the mechanical axis through sensing data from the trackable member 10'.

Various methods are considered for the digitization of a mechanical axis for the femur.

According to a first embodiment, an additional tracking member is temporarily secured to the femur at the entry point of the mechanical axis. By the weight of the patient, the pelvis of the patient is deemed to be in a fixed spatial position and orientation. The tracking member at the entry point of the mechanical axis, also known as a spike tracking member, is of the type equipped with tracking circuitry providing six-degree-of-freedom tracking data. With the tracking member at the entry point, a given motion about the center of rotation of the femur in the pelvis is performed (e.g., in a freehand manner). The motion can be continuous, or decomposed in several displacements with stable positions in between them. The tracking data resulting from the given motion is used to calculate a position and orientation of the center of rotation of the femur. The mechanical axis is then defined as passing through the center of rotation and the entry point (i.e., the spike tracking member). The orientation of the mechanical axis is transferred to the tracking member 10'. The spike tracking member may then be removed, with MEMS tracking member 10' kept on the femur for the subsequent tracking of the mechanical axis of the femur.

Figure 14:
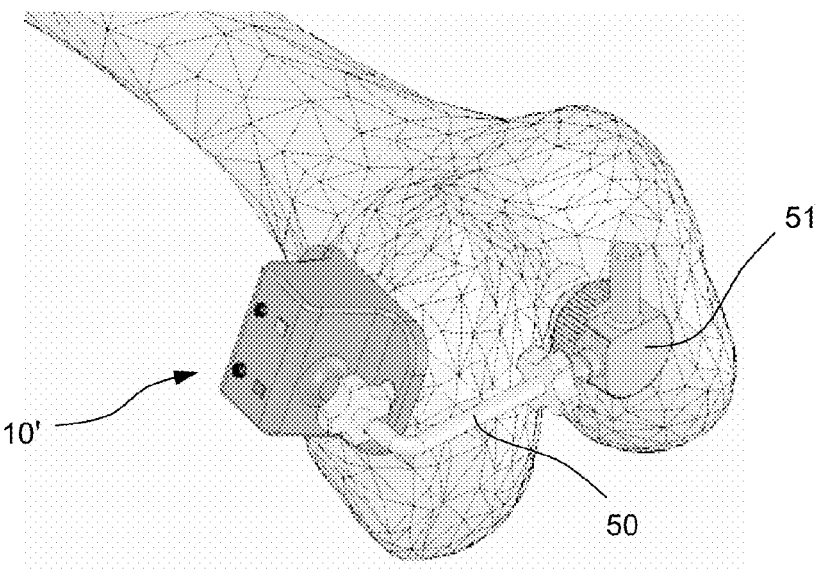
FIG. 14 is a perspective view of a tracking member and spike tracking member on the femur, in accordance with another embodiment of the present application.

Referring to FIG. 14, as an alternative to having a MEMS unit in the spike tracking member, a rigid link 50 may be provided between the spike 51 and the tracking member 10'. In this case, the geometry of the rigid link 50 is known such that the orientation of the spike 51 is calculable as a function of the tracking data from the tracking member 10'. Once the orientation of the mechanical axis of the femur is known and transferred to the tracking member 10', the rigid link 50 and spike 51 may be removed form the femur.

Figure 16:
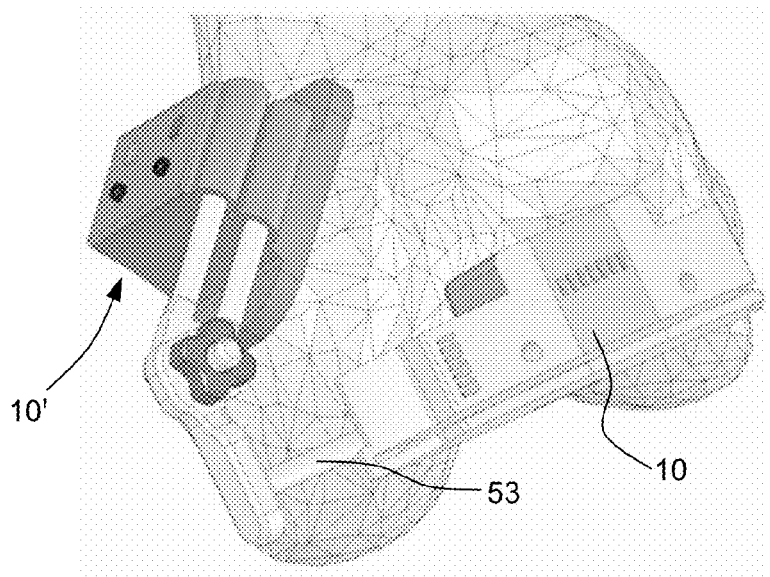
FIG. 16 is a perspective view of the cutting guide as related to the tracking member.

Alternatively, the spike 51 may be used as an alternative to the polyaxial screw to which the cutting guide 10 will be anchored. As the orientation and possibly the position of the spike 51/51' are known, the orientation of the cutting guide 10 may be known as a function of the tracking of the tracking member 10'. Referring to FIG. 16, the spike 51' may be removed while the cutting guide 10 remains in place.

In a second embodiment, the spike tracking member has tracking circuitry producing at least two-degree-of-freedom tracking data and linear accelerations along three orthogonal axes. The spike tracking member 51' (FIG. 15) is positioned at the entry point of the mechanical axis on the femur. In order to find the center of rotation, accelerative motions are performed according to a freehand or constrained trajectory for the distal part of the femur with respect to the immoveable pelvis. This trajectory can be spherical, linear or any other suitable pattern. An orientation of the mechanical axis may then be computed from the tracked accelerations and/or orientations of the femur. Once the orientation of the mechanical axis is known, the orientation of the mechanical axis is transferred to tracking member 10' and the spike tracking member is removed, and the tracking member 10' is tracked so as to follow the orientation of the mechanical axis of the femur. As an alternative to having a MEMS unit in the spike tracking member, a rigid link may be provided between the spike and the tracking member 10', as illustrated in FIG. 14. In this case, the geometry of the rigid link is known such that the orientation of the spike is calculable as a function of the tracking data from the tracking member 10'. Once the orientation of the mechanical axis of the femur is known and transferred to the tracking member 10', the rigid link and spike may be removed from the femur.

In yet another embodiment, a three-axis force sensor is positioned at the entry point of the mechanical axis of the femur. A force is applied to the three-axis force sensor, which force is measured by the three-axis force sensor. The measurement of the force enables calculation of the orientation of the mechanical axis of the femur. The force sensor may then be removed, whereby the tracking member 10' tracks the orientation of the mechanical axis.

In yet another embodiment, the orientation of the mechanical axis is determined using the tracking member 10', and by fixing the femur at its femoral center of rotation and at the entry point of the mechanical axis. A rotation about these two fixed points is then performed, which rotation is therefore about the mechanical axis of the femur. With the variation in orientation of the tracking member 10', the orientation of the mechanical axis is calculated with respect to the tracking member 10', from the tracking data.

Reference is made above to the entry point of the mechanical axis of the femur. The entry point of the mechanical axis is known to be in the depression above the inter-condylar notch region of the knee. As an alternative, it is considered to use a template to align the entry point with the center of the medio-lateral axis of the femur at the knee.

Various methods are considered for the digitization of a rotational axis for the femur.

According to a first embodiment, the rotational axis of the bone can be determined with the aid of an axis digitization device. The spike tracking member 51/51' may be equipped with two flat surfaces that can be simultaneously placed under both posterior condyles while the spike tracking member 51/51' is being inserted at the entry point of the mechanical axis. The axis-digitization device can be aligned either visually or mechanically with bone landmarks.

In a second embodiment, the knee joint is moved in a flexion and extension motion. Such motion can be continuous, or decomposed in several displacements with stable positions in between them. From the tracked orientation of the tracking members 10' of the tibia and femur, the orientation of the rotation axis of the femur can be determined.

In yet another embodiment, the knee is be positioned in 90 degrees of flexion. From the orientation of the tracking members 10' of the tibia and the femur, along with the previously digitized mechanical axis of the tibia, the rotational axis of the femur can be computed.

In yet another embodiment, the leg is positioned in full extension so that the rotational axes of the femur and tibia are aligned. From the orientation of the tracked members of both bones, and the previously digitized rotational axis of the tibia, the rotational axis of the femur can be computed.

With the rotational axis and the mechanical axis, a plane incorporating the mechanical axis is known. This data is used as an orientation reference for the subsequent calculation of parameters.

According to step 4, the positioning block 10 is then secured to the femur at the central point between the condyles, as set forth in United States Publication No. 2008/0065084, and United States Publication No. 2004/0039396. The positioning block 10 may be installed on the femur prior to step 3. Other configurations of positioning blocks may be used, such as the ones shown in FIGS. 9 and 10 and in FIGS. 12 and 13 and described in further detail hereinafter. It is considered to have the tracking member 10' on the fixed portion of the positioning block 10.

It is pointed out that steps 2 and 3 of the method are part of step 4 when the positioning block has MEMS on both its fixed portion and movable portion, as described above. More specifically, the MEMS is secured to the bone (i.e., step 2) when the positioning block is secured to the bone, and both MEMS provide orientation data simultaneously.

According to step 5, the positioning block 10 is calibrated with respect to the mechanical axis. More specifically, the positioning block 10 defines planes that will be used to guide the operator in resecting the bone, and these planes are aligned with respect to the mechanical axis. The orientation of the mechanical axis may be validated. A validation tool (not shown) may be used by being applied to the posterior condyles of the distal femur. A rotation about the posterior condyles is tracked relative to the tracking member 10', and used as rotational information when distal cuts are performed on the femur.

Figure 2:
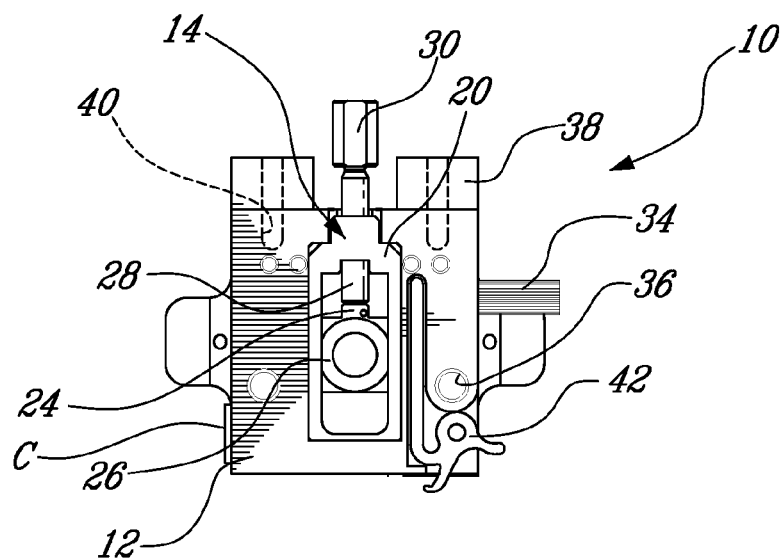
FIG. 2 is a front elevation view of the universal positioning block of FIG. 1.
Figure 4A:
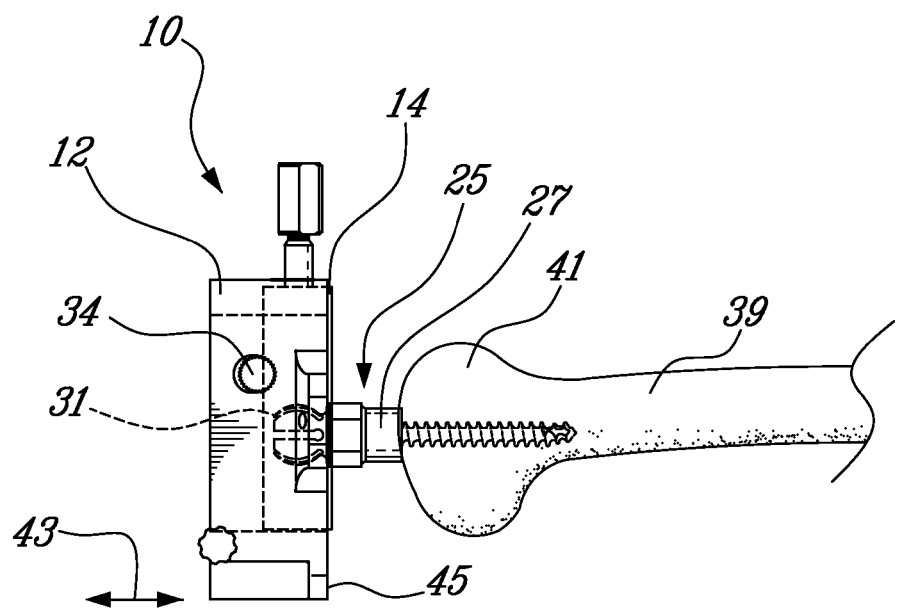
FIG. 4A is a side elevation view of the universal positioning block of FIG. 1 mounted to a femur.
Figure 4B:
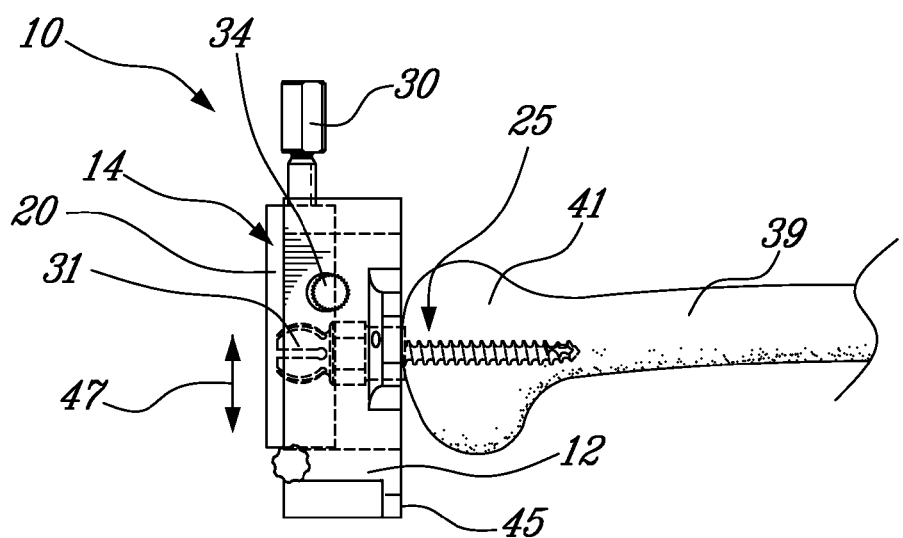
FIG. 4B is a side elevation view of the universal positioning block of FIG. 1 mounted to a femur and the positioning body proximally displaced such that it abuts the femur.

FIGS. 4A and 4B show the universal positioning block assembly 10 mounted to the distal end of a femur 39 by the polyaxial screw 25. The degree of mobility of the universal positioning block 10 permits significant simplification of the surgical procedures employed in certain surgeries, such as total knee replacement surgery. As shown in FIG. 4A and in step 4 of FIG. 5, the fastening of the positioning block 10 to the bone B is preferably done using the polyaxial screw 25, which is first aligned with the entrance point of the mechanical axis at the distal end of the femur and introduced therein until its shoulder 27 touches the bone. The fastener mount element 24 of the universal positioning block 10, as best seen in FIG. 1 and FIG. 2, is snapped onto the head 31 of the polyaxial screw. As mentioned previously, to reduce the invasiveness of the procedure, the tracking member 10' and the positioning block 10 may be interconnected. The tracking member 10' would be on the fixed portion of the positioning block 10'. According to this embodiment, no polyaxial screw would be required.

It is considered to align the positioning block with the posterior condyles, using the validation tool described above. It is also considered to align the positioning block 10 such that the positioning block 10 is aligned with the anterior-posterior axis of the femur. More specifically, the anterior-posterior axis of the femur is visually identifiable at the knee by an anterior point and a posterior point, namely the trochlear groove (Whiteside's line) or, alternatively, the anterior-posterior axis may be aligned to the plane perpendicular to both posterior condyles. Therefore, when the positioning block 10 is secured to the femur, with the anterior-posterior axes being aligned, the adjustments in orientation of the positioning block with respect to the femur are limited to flexion-extension and varus-valgus, which may be adjusted independently from one another. The positioning block 10 can also be positioned with respect to a rotation relative to the anterior-posterior axis or the posterior condyles.

According to step 6, an orientation of the positioning block 10 is manually adjusted, as a function of the alterations to be performed on the femur. For instance, the various screws on the positioning block 10 are used to adjust the orientation of the block, with varus/valgus and flexion/extension being adjusted independently from one another as a result of a previous calibration of the orientation of the positioning block 10 on the bone (step 5).

Step 6 of determining a desired position of the positioning block 10, or a portion thereof such as a reference surface 45 on the guide body 12, is done either by the CAS system itself, by the surgeon using the CAS system as a guide or independently by the surgeon, in order to determine what final position the positioning block 10 should be moved into such that a drilled hole or a sawn cut can be made in the bone element at a predetermined location that is required for the installation of an implant. Step 6 comprises adjusting the orientation of the positioning block 10 until it, or a portion thereof such as the reference surface 45 of the guide body 12, is located in the desired orientation. This can involve rotatably adjusting the positioning block 10 relative to the bone element, using the tracking information to aid in the correct orientation in each axis of rotation. Three rotational degrees of freedom are thereby possible, and the entire positioning block 10 can be oriented in a desired plane, for example parallel to the distal cut to be made in the femur. Step 4 can also include proximally displacing the positioning block 10 in the direction 43 such that the proximal surface 45 is translated from a position shown in FIG. 4A to a position shown in FIG. 4B, abutting the femur 39. As the head 31 of the polyaxial screw 25 is distally spaced from the condyles 41 of the femur 39, the positioning block 10 requires a reference point with respect to the bone such that the location of the distal cutting guide, which will be fixed to the positioning guide block, will correctly correspond to the amount of bone which must be resected by the distal cut.

The proximal-distal translation of the guide block body 12 relative to the mounting member 14 simplifies the referencing of the guide block with the femur. As the mounting member 14 is engaged in place on the head of the polyaxial screw, it is fixed in a proximal-distal direction relative to the bone. However, as the guide block body 12 can axially slide relative to the central mounting member 14 when the locking screw 34 is disengaged, the tracked guide body portion 12 remains rotationally fixed relative to the mounting member 14 but can translate in the proximal-distal direction 43. This permits the guide body 12 to be proximally displaced until its proximal surface 45 directly abuts the most distal end of the condyles 41, as shown in FIG. 4B. By tightening the locking screw 34, the guide body 20 is retained in place on the central mounting member 14. The conical screw 33, as seen in FIG. 3, when tightened, fixes the positioning block 10 in place on the head 31 of the polyaxial screw 25, thereby fixing the reference surface 45 in the chosen desired position. The distal end of the femur, which is accurately located by the tracked guide body 20 that is located by the CAS system, can then be used as a reference plane, from which the resection depth can be easily measured. The amount of bone resected often varies as a function of the type of implant line being used, and the specific structure of the patient anatomy.

Further adjustment is also possible with the present universal positioning block assembly 10. Step 6 of FIG. 5 also comprises translation of the entire positioning block assembly 10 relative to the polyaxial screw 25, and therefore relative to the femur, in the anterior-posterior direction 47. By rotating the screw head 30, the mounting member body 20, shown in FIG. 2, and consequently the entire guide block body 12 are displaced relative to the fastener mount element 24 that is fixed to the polyaxial screw head 31. This affords substantially vertical adjustment of the positioning block if required by the specific procedure or the anatomy of the patient being operated. The positioning block can therefore be adjusted in five degrees of freedom, namely rotation about three rotational axes and translation along two perpendicular axes, namely in directions 43 and 47 and in rotation if needed.

According to step 7, alteration parameters such as varus/valgus and flexion/extension and rotation are provided as calculated by the CAS as a function of the adjustments to the orientation of the positioning block 10. The CAS receives the tracking of the mechanical axis from the tracker member 10', as well as the orientation changes from the MEMS tracking circuitry on the positioning block 10. Therefore, the CAS deducts motion of the femur from the orientation changes of the positioning block 10 to calculate the implant parameters. The amount of varus/valgus and flexion/extension is updated in real-time on the positioning block and displayed to the surgeon by a simple graphical means. For example, an array of Light-Emitting Diodes (LEDs) can be positioned on the positioning block or within the field of view of the surgeon, such that a green light may be turned on when the angle is appropriate and stays red as long as the orientation is not appropriate in a particular plane.

Once a desired orientation is set, the positioning block 10 is used to guide the operator in resecting the femur as set forth in United States Publication No. 2008/0065084, and in United States Publication No. 2004/0039396.

If no tracker member 10' is used on the femur during the cutting procedure, it could still be installed after the cut has been made in order to provide hip-knee-ankle angle (i.e., HKA) information later on during the procedure. Once the cut has been made, a tracker member 10' would then be fixed to the femur and all coordinate system information registered to this tracker member 10' for further measurements, such as HKA.

It is considered to use the positioning block to confirm the cut planes of the femur at the knee. More specifically, as the orientation of the positioning block 10 is known in all three degrees of freedom, the positioning block 10 may simply be brought into contact with the various surfaces of the knee so as to obtain an orientation of the cut planes with respect to the tracking member 10' and thus as a function of the mechanical axis of the femur. This allows the measurement of any deviations that may occur during the cutting process.

Figure 15:
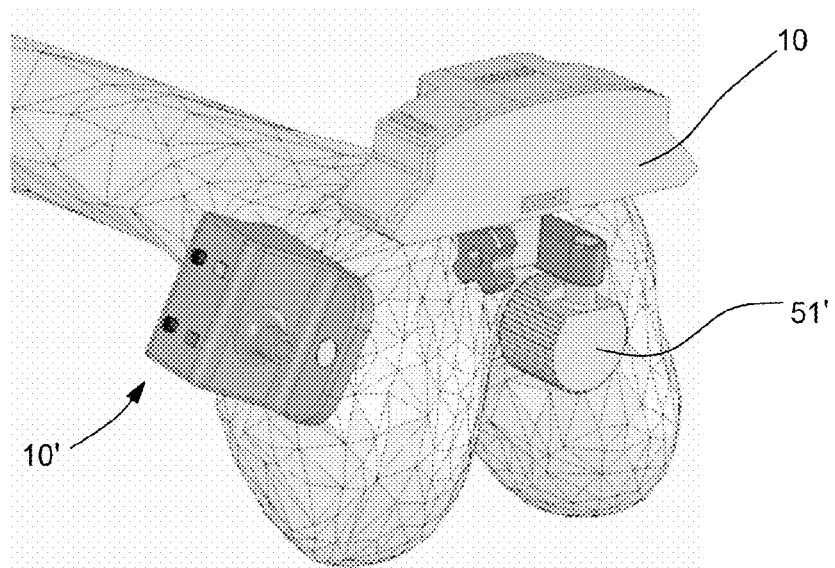
FIG. 15 is a perspective view of spike tracking member supporting a cutting guide.
Figure 17:
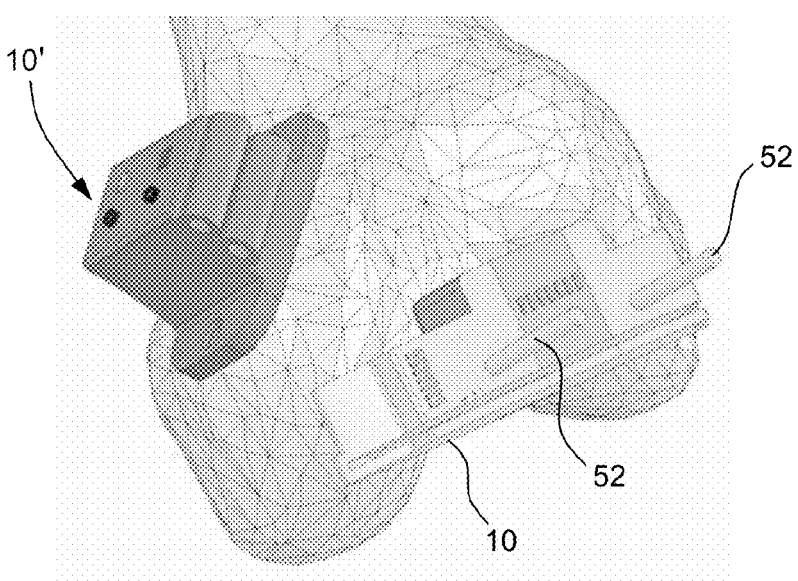
FIG. 17 is a perspective view of the cutting guide pinned to the femur.

Referring to FIGS. 15 to 17, different configurations are illustrated for the positioning block 10, tracking member 10' and spike tracking member 51' with MEMS. In FIG. 15, there is illustrated the positioning block 10 being connected to the tracking member 51'. In this case, the spike tracking member 51' forms a rigid link with the positioning block 10, whereby an orientation tracking of the positioning block 10 is possible from the tracking data of the spike tracking member 51'.

Referring to FIG. 16, a linkage 53 is provided between the tracking member 10' and the positioning block 10. Therefore, once the orientation of the positioning block 10 is tracked with respect to the mechanical axis or other reference of the femur, the linkage 53 allows the finer adjustment of the orientation of the positioning block 10 with respect to the femur. The positioning block 10 features visual indicators, such as flexion-extension and varus-valgus, in view of a plane being cut in the bone using the positioning block 10. Referring to FIG. 17, once suitable parameters are attained (e.g., varus-valgus, flexion-extension, etc.), the positioning block 10 is anchored to the femur, for instance using the pins 52.

The method 1 is now described as used to plan alterations on the tibia at the knee.

According to step 2, the MEMS trackable member 10' is secured to the tibia (or soft tissue) so as to be in a fixed relation with respect to the tibia. Another MEMS trackable member could be used, with a shape that is more appropriate for use with the tibia.

Alternatively, the trackable member 10' could be eliminated if dynamic tracking is not used because the tibia or the femur is immobilized and all tracking is performed via the MEMS positioning block 10, as described above.

According to step 3 of the method, an axis of the tibia is digitized. The axis is, for instance, the mechanical axis of the tibia. According to a first embodiment, in order to digitize the mechanical axis, the tibia is moved about a reference point and the movements are sensed by the MEMS tracking member 10' on the tibia. From the sensing data collected by the MEMS tracker member 10' secured to the tibia, the computer-assisted surgery system digitizes the mechanical axis of the tibia and tracks the mechanical axis through sensing data from the trackable member 10'. Whether it be for the femur or the tibia, the axes may be digitized in a freehand manner by the operator, for instance using a fixed visual reference point, or relying on the operator's skill to minimize given movements of the bone during step 3.

Figure 8:
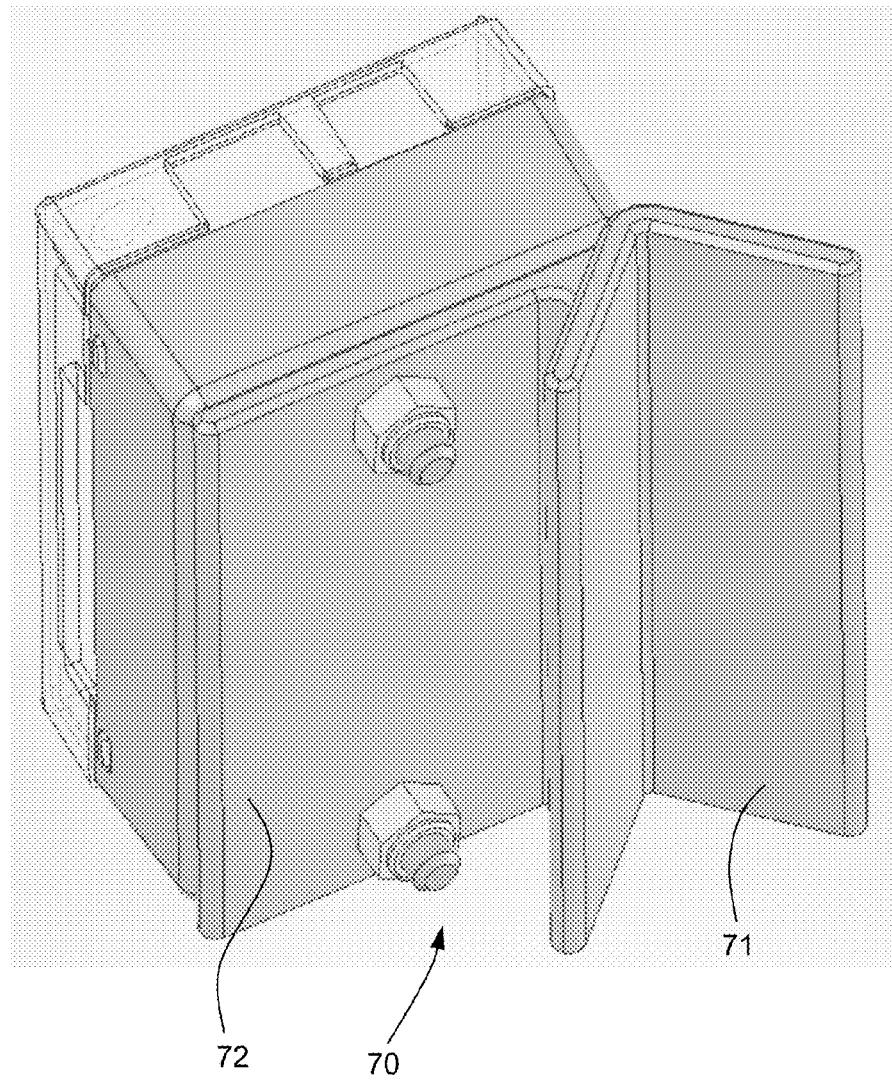
FIG. 8 is a perspective view of an axis-digitizing device as used in the computer-assisted surgery system of the present application, in accordance with a first embodiment.

In a second embodiment, referring to FIG. 8, an axis-digitizing device 70 is illustrated, and may be used to determine the mechanical axis of the tibia. The axis-digitizing device 70 has a trough 71 and a MEMS unit 72. The trough 71 is positioned on the anterior crest of the tibia, for instance, directly on the soft tissue, which happens to be relatively thin on the anterior crest of the tibia. Also, the middle point of the tibial plateau (from medial to lateral) can be connected to the middle point of the ankle joint with self-centering devices. The middle point of the tibial plateau can be connected to the $2^{nd}$ metatarsal bone via a guide rod or a laser pointing device. It must be ensured that there is no relative movement between the device 70 and the tibia during step 3. This is readily accomplished since the registration process is performed relatively quickly. The MEMS unit 72 is typically equipped with two-degree-of-freedom or three-degree-of-freedom tracking circuitry, or calibrated to perform orientation tracking.

Various methods are considered for the digitization of a rotational axis for the tibia.

According to a first embodiment, the rotational axis of the bone can be determined with the aid of an axis digitization device, such as the axis digitizing device 70 (FIG. 8), or any other suitable device. The axis-digitization device can be aligned either visually or mechanically with bone landmarks.

In a second embodiment, the knee joint is moved in a flexion and extension motion. Such motion can be continuous, or decomposed in several displacements with stable positions in between them. From the tracked orientation of the tracking members 10' of the tibia and femur, the orientation of the rotation axis of the tibia can be determined.

In yet another embodiment, the knee is be positioned in 90 degrees of flexion. From the orientation of the tracked members of the tibia and the femur, along with the previously digitized mechanical axis of the femur, the rotational axis of the tibia can be computed.

In yet another embodiment, the leg is positioned in full extension so that the rotational axes of the femur and tibia are aligned. From the orientation of the tracked members of both bones, and the previously digitized rotational axis of the femur, the rotational axis of the tibia can be computed. The rotational axis and the mechanical axis are combined to form an orientation reference for the calculation of alteration parameters.

According to step 4, the positioning block 10 is then secured to the tibia at a desired position, as set forth in United States Publication No. 2008/0065084, and United States Publication No. 2004/0039396. It is pointed out that the positioning block 10 may be installed on the tibia prior to step 3.

Figure 9:
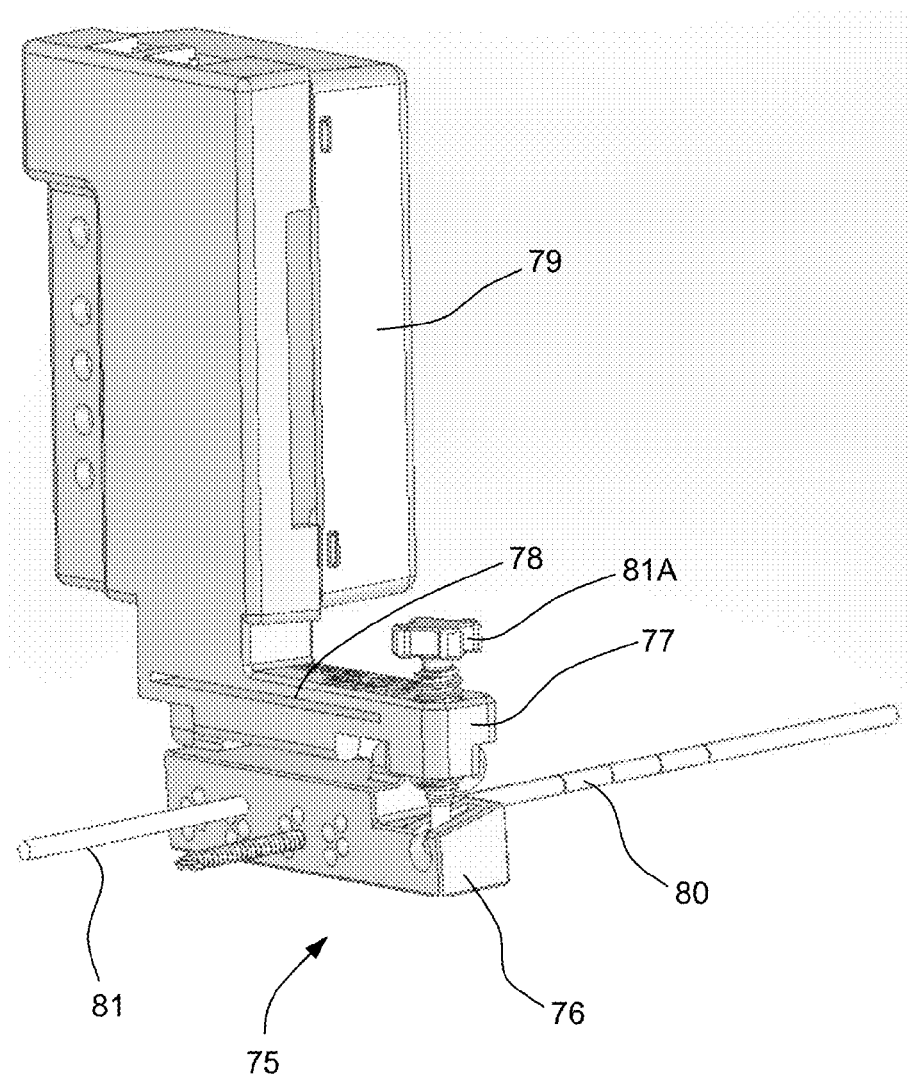
FIG. 9 is a perspective view of a positioning block in accordance with another embodiment of the present application.
Figure 10:
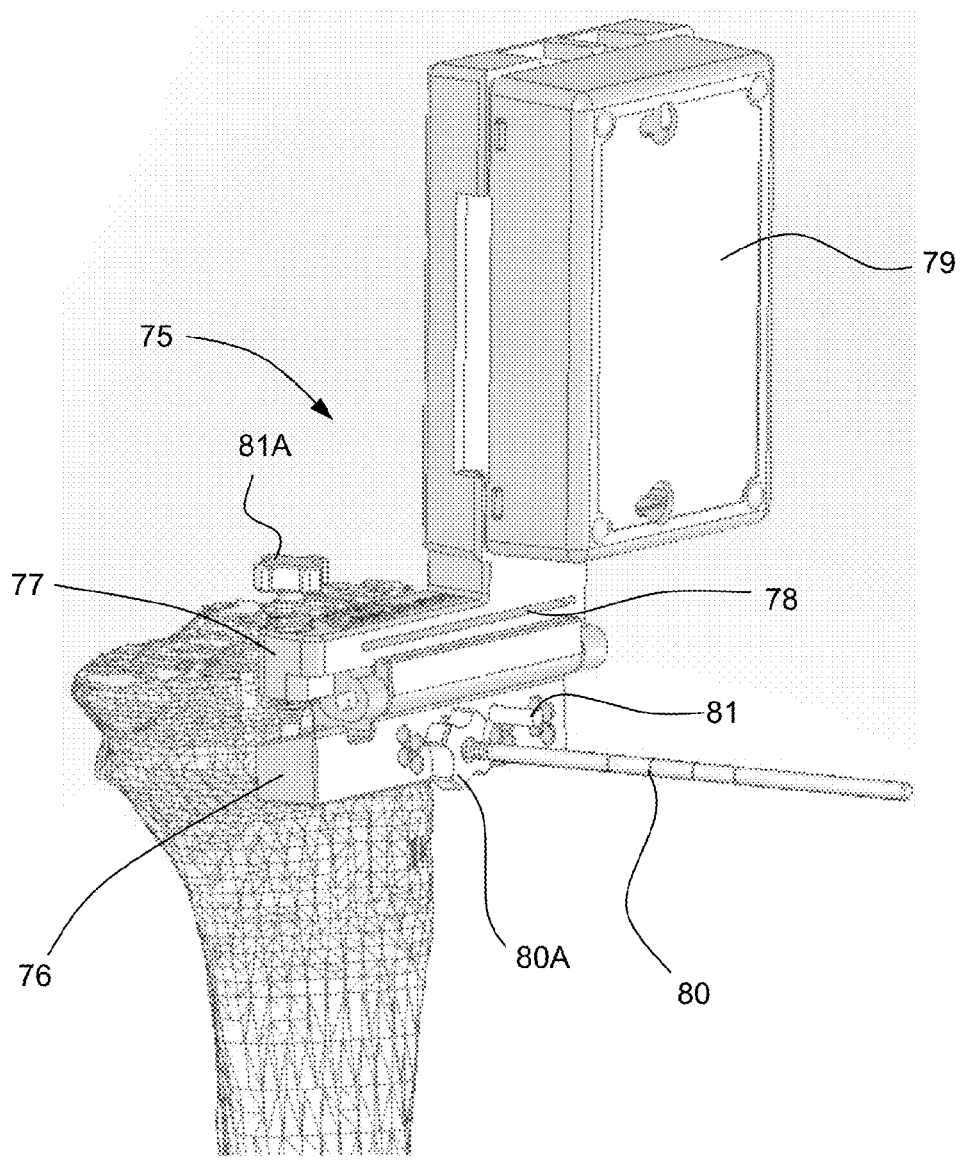
FIG. 10 is a perspective view of the positioning block of FIG. 9 as mounted to a bone.

An alternative embodiment of the positioning block is illustrated at 75 in FIGS. 9 and 10. When the positioning block 75 is secured to the tibia, the anterior-posterior axis of the positioning block 75 is aligned with that of the tibia. More specifically, points that can be used to visually identify the anterior-posterior axis of the tibia are the connection point of the posterior cruciate ligament, and the medial third tubercle. Other anatomical landmarks that can be used to define the tibia anterior-posterior axis are described hereinafter. The axis perpendicular to the line joining the most posterior points of the tibia plateau is a first alternative to the tubercle-PCL axis. Secondly, a kinematic analysis performed between the femur and the tibia, in flexion-extension, can give a unique flexion-extension axis where the perpendicular can be used as another alternative to the previously described AP axis. Similarly, the axis perpendicular to the femoral posterior condyle axis can be projected on the tibia, when the leg is in full extension, and used again as the third options. Another alternative AP landmark would be the projection of the femoral mechanical axis on the tibia, when the leg is in pure flexion i.e. 90 degrees.

With the positioning block 75 being secured to the tibia with the anterior-posterior axes of the tibia and the positioning block being aligned, the positioning block 10/75 may only be moved in the flexion-extension orientation and in the varus-valgus orientation.

The positioning block 75 has a base 76 that is fixedly secured to the bone. A cutting guide 77 is pivotally mounted to the base 76 by a pivot joint. The cutting guide 77 has a slot 78 into which a blade is inserted to perform cuts on the tibia. A MEMS unit 77 is integral with the cutting guide 77 so as to track the orientation of the cutting planes, and provides 3-DOF tracking to provide tracking data related to the orientation of the cutting guide 77. The positioning block 75 is secured to the bone by a first threaded rod 80. Once a desired varus-valgus orientation is reached using knob 80A (FIG. 10), rod 81 is used so as to secure the base 76 to the bone in the varus-valgus orientation. The flexion-extension orientation is then adjusted using knob 81A so as to reach a desired orientation of the cutting guide 77 in view of creating the cutting planes on the tibia. It is pointed out that the virtual cut planes may be tracked as a function of the geometry of the slot 78 in the positioning block 75. More specifically, the MEMS unit 75, or the processing system 101 may be provide with the data representing the cut planes, such that secondary cut planes can be tracked to simulate the positioning of an implant on the bone.

According to step 5, the positioning block 10 is calibrated with respect to the mechanical axis. More specifically, the positioning block 10 defines planes that will be used to guide the operator in resecting the bone, and these planes are aligned with the mechanical axis.

According to step 6, an orientation of the positioning block 10 is manually adjusted, as a function of the alterations to be performed on the tibia.

According to step 7, alteration parameters such as varus/valgus, and flexion/extension are provided as calculated by the CAS as a function of the manual adjustments to orientation of the positioning block 10. The CAS receives the tracking of the mechanical axis from the tracker member 10', as well as the orientation changes from the MEMS tracking circuitry on the positioning block 10. Therefore, the CAS deducts motion of the tibia from the orientation changes of the tracking circuitry to calculate the implant parameters. The amount of varus/valgus and flexion/extension is updated in real-time on the positioning block and displayed to the surgeon by a simple graphical means. For example, an array of light-emitting diodes (LEDs) can be positioned on the positioning block or in the field of view of the surgeon such that a green light goes on when the angle is appropriate and stays red as long as the orientation is not appropriate in a particular plane.

Alternatively, the tracker member 10' could be eliminated from the procedure, relying exclusively on the positioning block 10 to obtain mechanical axis information.

If no tracker member 10' was used on the tibia during the cutting procedure, it could still be installed after the cut has been made in order to provide HKA information later on during the procedure. Once the cut has been made, a tracker member 10' would then be fixed to the tibia and all coordinate system information registered to this tracker member 10' for further measurements, such as HKA.

Once the planes have been cut in the tibia, the positioning block may be used to digitize the orientation of the cut planes with respect to the mechanical axis of the tibia. More specifically, as the positioning block 75 is tracked for orientation by the MEMS unit 79, the positioning block 75 may simply be laid upon the cut planes so as to digitize an orientation of such planes with respect to the mechanical axis of the tibia.

Once a desired orientation is set, the positioning block 10 is used to guide the operator in resecting the tibia as set forth in United States Publication No. 2008/0065084, and United States Publication No. 2004/0039396.

As additional information, the MEMS trackable members 10' on the femur and the tibia may be used concurrently to determine the HKA by lying the leg flat on a table. Alternatively, the femur and tibia may be held in complete extension, with the leg held at an angle in space. Such a maneuver is simply accomplished by lifting the whole leg while holding it from the talus. The micro-circuitry of tracking members installed on the tibia and femur may be providing rotational information using at least one three DOF sensor, such as a gyroscopic sensor. In such a case, the gyroscopic sensor can provide alignment information of the femur relative to the tibia.

Referring to FIG. 6, a MEMS positioning block 10 and a MEMS trackable member 10' in accordance with an embodiment of the present application are generally shown as being fixed to a bodily element such as a bone B.

The MEMS positioning block 10 and the MEMS trackable member 10' are used with a tracking CAS system and comprises tracking circuitry, and optionally a wireless transmitter (or like communication circuitry). The block 10 and member 10' may be wired to the CAS system as well.

In an embodiment of the present disclosure, the tracking circuitry is known as a two-degree-of-freedom (hereinafter DOF) micro-circuitry, but may alternatively provide data for more than three DOFs. The tracking circuitry of the MEMS positioning block 10 and the MEMS trackable member 10' outputs orientation-based data pertaining to the bone B.

As an alternative embodiment, transmitters are connected to the tracking circuitry of the MEMS positioning block 10 and the MEMS trackable member 10' so as to transmit the tracking data of the tracking circuitry 10 to the processing system of the CAS system 100. The technology used for the transmitter 10' is selected to operate in a surgical environment, such as RF. As an example, Bluetooth™, Zigbee™ or Wi-Fi transmitters are considered for their wide availability. The MEMS can be manufactured as a single disposable unit, possibly integrated to the positioning block 10 and to the trackable member 10'. As an alternative embodiment, sensors can be configured to communicate necessary information between themselves.

Referring to FIG. 6, a tracking computer-assisted surgery system incorporating the MEMS positioning block 10 and the MEMS trackable member 10' is generally illustrated at 100. The computer-assisted surgery system (CAS system) has a processing system 101, which typically comprises a computer having a processor. A receiver 102 is provided in the processing system 101 so as to receive the orientation-based data signal from the MEMS positioning block 10 and the MEMS trackable member 10'. Alternatively, the MEMS positioning block 10 and the MEMS trackable member 21 are wired to the processing system 101.

A controller 103 is connected to the receiver 102 or is wired to the MEMS positioning block 10 and the MEMS trackable member 10'. Therefore, the controller 103 receives the signal data from the receiver 102 or from the MEMS positioning block 10 and the MEMS trackable member 10'.

A signal interpreter 104 is used to convert the signal data received into orientation data for the MEMS positioning block 10 and the MEMS trackable member 10'.

A geometry database 105 is provided in order to store the calibration data, and other intraoperative data such as the mechanical axis defined intraoperatively. The calibration data is therefore relational data between the bone B, the MEMS positioning block 10 and the MEMS trackable member 10'.

A parameter calculator 106 is associated with the controller 103. The parameter calculator 106 receives the orientation data from the signal interpreter 104, and the relational data from the geometry database 105. With the relational data provided by the database 105, the parameter calculator 106 calculates alteration parameters as a function of the orientation of the positioning block 10 with respect to the bone B, such as varus/valgus and flexion/extension and the like, depending on the application. Accordingly, the controller 103 outputs alteration parameters to the user interface 110.

In an embodiment, either one of the MEMS positioning block 10 and the MEMS trackable member 10' has a self-enclosed processing unit connected to the tracking circuitry. The MEMS positioning block 10 or the MEMS trackable member 10' has the tracking circuitry, a transmitter/receiver and also the processing system 101, all in a compact self-enclosed casing. Accordingly, the transmitter/receiver 10' is used to share information with other one of the MEMS positioning block 10 and the MEMS trackable member 10' used concurrently during the surgical procedure.

In such an embodiment, the alteration parameters are displayed directly on the positioning block 10 or on the trackable member 10'. It is considered to use a set of LEDs or another form of compact electronic display (e.g., LCD) as user interface 1, to minimize the size of the self-enclosed casing.

Figure 7:
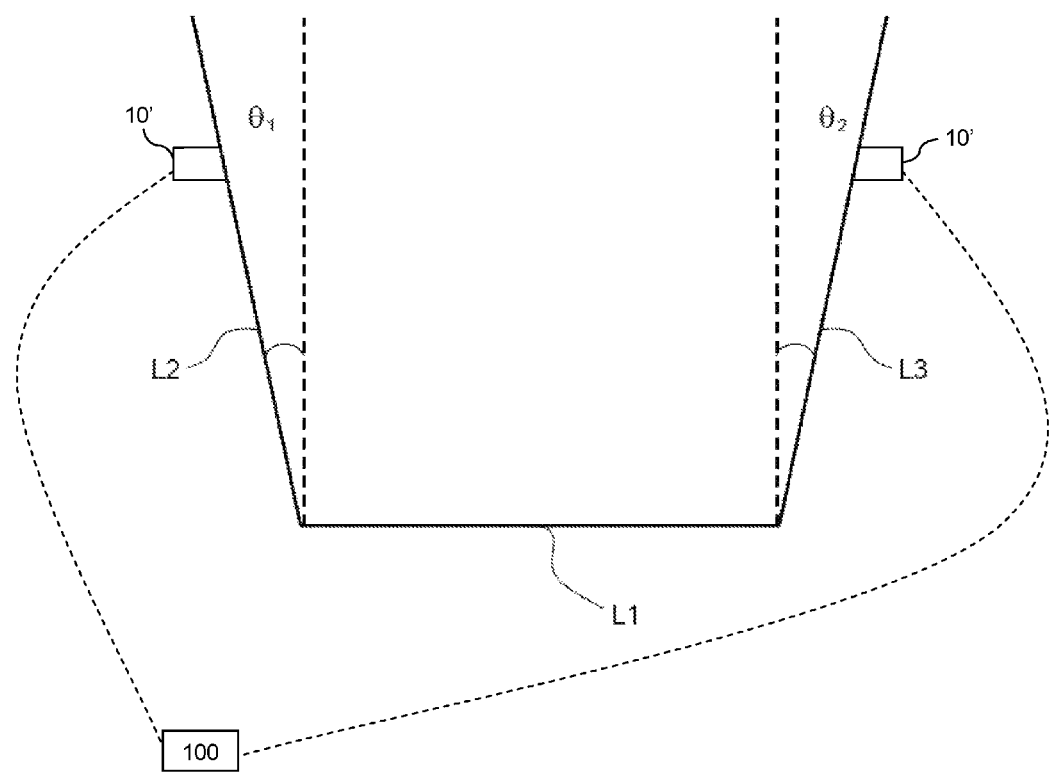
FIG. 7 is a schematic view of a caliper in accordance with another embodiment of the present disclosure.

Referring to FIG. 7, a caliper in accordance with another embodiment is generally shown having a base L1, and arms L2 and L3. The caliper is used to determine length of objects using tracking circuitry such as MEMS. More specifically, the length of the base L1 is known, as is the lengths of the arms L2 and L3.

The arms L2 and L3 are pivotally mounted to ends of the base L1. The free ends of the arms L2 and L3 are used to identify a limit point of the object to measure. In other words, the distance measured is the distance between the free ends of the arms L2 and L3.

The tracking circuits 10' are secured to the arms L2 and L3, and produce orientation data pertaining to an orientation of the arms L2 and L3 in a plane in which the arms and the base L1 lie. The orientation data is illustrated as θ1 and θ2. Accordingly, the distance is calculated using: L1 +L2 sin (θ1)+L3 sin(θ2). The caliper may have a single arm L2 and base L1 (i.e., no L3, simply removed from FIG. 7). In such a case, the angle between the arm L2 the and base L1 along with their lengths are used in basic trigonometry to calculate the distance between the tips of L1 and L2.

The tracking circuitry is connected to the CAS system, or wirelessly transmits data to a CAS system. Moreover, it is considered to provide a tracking circuit on the base L1 as well, so as to obtain the orientation changes of the arms L2 and L3 relative to the base L1.

The MEMS positioning block 10, the MEMS trackable member 10' (FIG. 6) and the caliper (FIG. 7) may be disposable, reusable after sterilization, or returnable for refurbishment and resterilization by the manufacturer.

Figure 11:
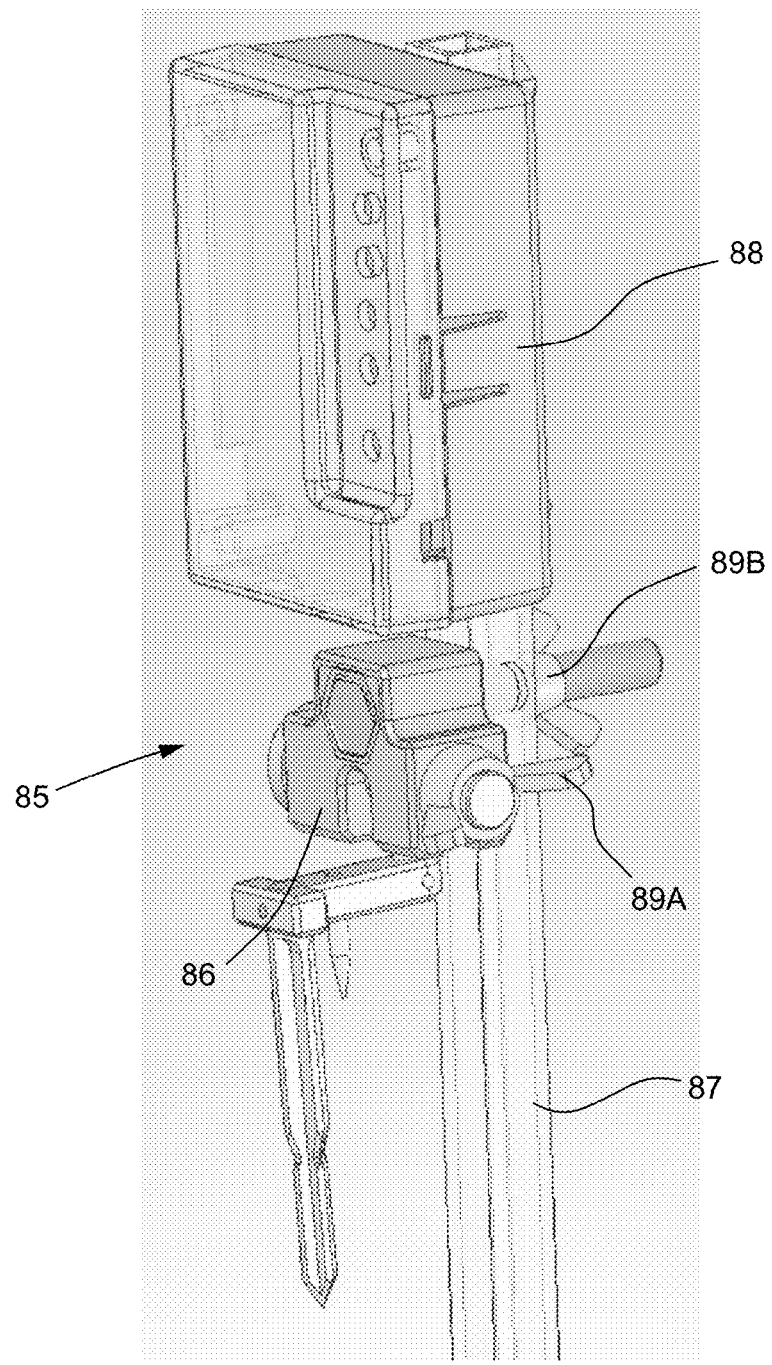
FIG. 11 is a perspective view of an axis-digitizing device used with the computer-assisted surgery system of the present application, in accordance with another embodiment.

Referring to FIG. 11, an axis-digitizing device is generally shown at 85. The axis-digitizing device 85 may be used as an alternative to the axis-digitizing device 70 of FIG. 8. The device 85 has a base 86 that anchors to the tibia at the knee so as to be aligned with the anterior-posterior axis of the tibia, and features an alignment bar 87 projecting downwardly. The alignment bar 87 is to be aligned with the anterior crest of the medial third of the tibial tubercle. Alternatively, the bar 87 may be directed towards the $2^{nd}$ metatarsal bone. The device 85 may also be equipped with a self-centering mechanism at both ends, connecting to the center of the tibial plateau and to the center of the ankle joint. The MEMS unit 88 is integral with the alignment bar 87, whereby any change in orientation of the alignment bar 87 is trackable. Knobs 89A and 89B are used to adjust the orientation of the alignment bar 87 with respect to the tibia.

Figure 12:
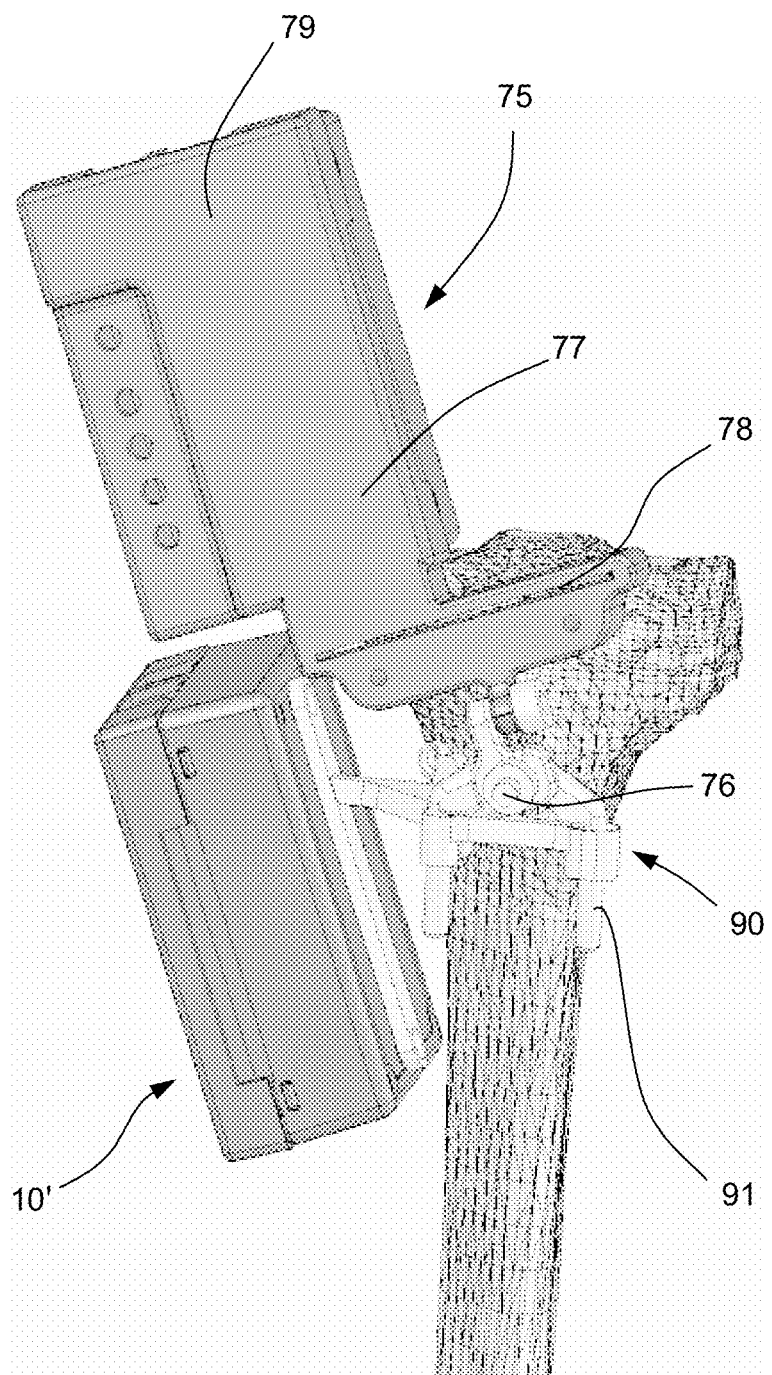
FIG. 12 is a perspective view of a positioning block with tracking member as secured to a tibia.
Figure 13:
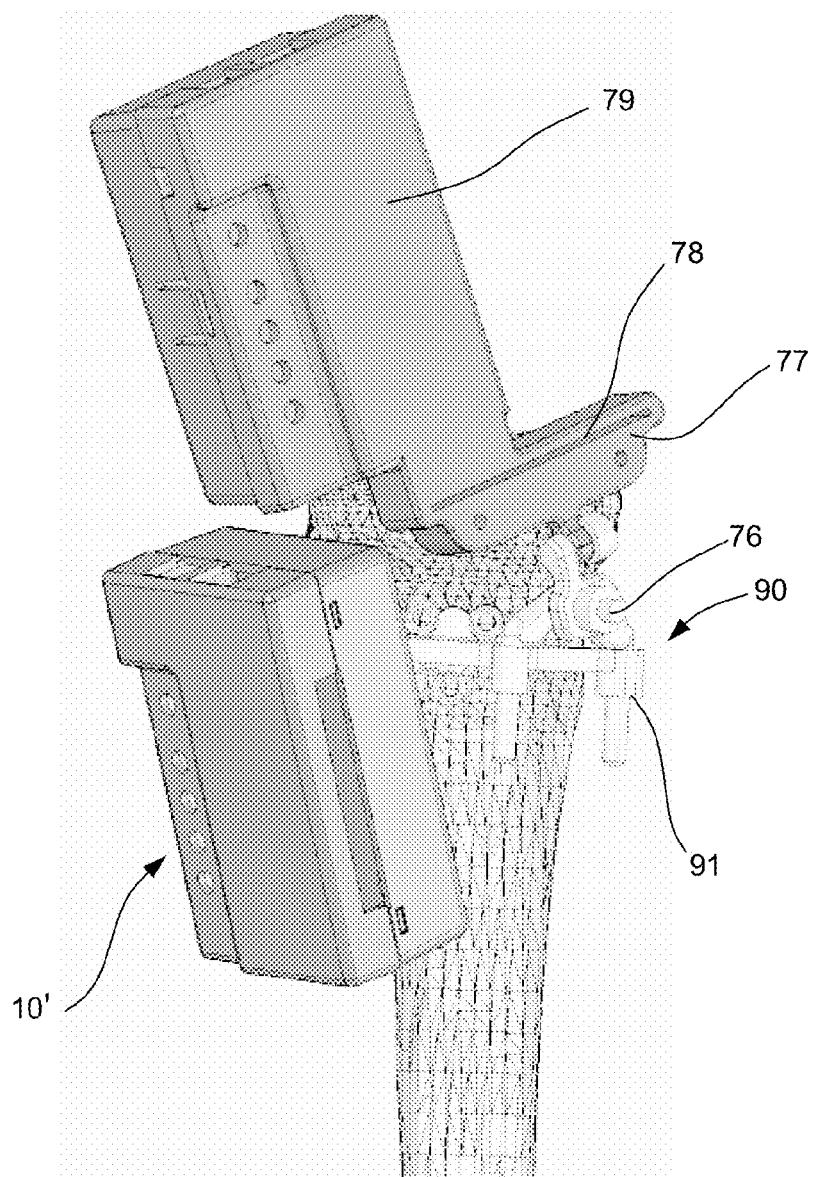
FIG. 13 is perspective view of the positioning block with tracking member of FIG. 12 from another standpoint.

Referring to FIGS. 12 and 13, a bracket 90 is shown as securing the tracking member 10' and the positioning block 75 to the tibia, in a non-invasive manner. A translational joint 91 is provided in the bracket 90 to ensure the vertical alignment of the positioning block 75 with respect to the knee. In FIG. 12, the bracket 90 has two rotational joints, to provide orientation adjustments of the positioning block 75. It is considered to use joint encoders to measure any rotation of the positioning block 75 with respect to the tracking member 10'. The joint encoders may be an alternative to the MEMS of the positioning block 75, or data to validate the information from the MEMS of the positioning block 75.

As yet another alternative, it is considered to allow the operator to adjust a position/orientation of the positioning block 10/75 in a freehand mode. In such a case, the alteration parameters are displayed while the positioning block 10/75 is displaced with respect to the bone, so as to allow the operator to select a position/orientation along these alteration parameters. Once an appropriate position/orientation the positioning block 10/75 is pinned to the bone.

The invention claimed is:

1. A caliper for determining a dimension of an object, comprising:
   a base having a known base length;
   at least one arm pivotally mounted to an end of the base, the arm having a known arm length, and having a free end used to identify a limit point of the object to measure;
   an inertial sensor unit secured to the at least one arm, the inertial sensor unit producing orientation data pertaining to at least one degree of freedom in orientation of the arm in a plane in which the at least one arm and the base lie;
   whereby the dimension between limit points is calculated from the known base length and the arm length and from the orientation data of the at least one arm relative to the base.

2. The caliper according to claim 1, comprising two of said arms with the free ends of the arms identifying the limit points of the object to measure, each said arm having an own one of the inertial sensor unit secured thereto.

3. The caliper according to claim 1, comprising one of said inertial sensor unit on one of the arms, and another one said inertial sensor unit on at least one of the other arm and the base.

* * * * *